(12) United States Patent
Khanuja et al.

(10) Patent No.: US 7,196,115 B2
(45) Date of Patent: Mar. 27, 2007

(54) PHARMACEUTICAL COMPOSITION CONTAINING BREVIFOLIOL FOR USE IN CHEMOTHERAPEUTIC TREATMENT OF HUMAN BEINGS, METHOD THEREFOR

(75) Inventors: Suman Preet Singh Khanuja, Uttar Pradesh (IN); Ranganathan Santha Kumar Tirupadiripuliyur, Uttar Pradesh (IN); Ankur Garg, Uttar Pradesh (IN); Raghvendra Kumar Mishra, Uttar Pradesh (IN); Sunil Kumar Chattopadhyay, Uttar Pradesh (IN); Sachin Srivastava, Uttar Pradesh (IN); Arvind Singh Negi, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/334,675

(22) Filed: Dec. 30, 2002

(65) Prior Publication Data
US 2004/0127561 A1 Jul. 1, 2004

(51) Int. Cl.
*A61K 3/21* (2006.01)
*A61K 31/335* (2006.01)
(52) U.S. Cl. .................. 514/510; 514/449; 424/9.2; 436/64
(58) Field of Classification Search .............. 514/510, 514/183, 449, 453, 454, 532, 885, 901; 424/769, 424/770
See application file for complete search history.

(56) References Cited
U.S. PATENT DOCUMENTS
5,407,683 A * 4/1995 Shively ............... 424/439

5,475,120 A * 12/1995 Rao .................. 549/510
5,919,816 A * 7/1999 Hausheer et al. ........ 514/449
6,333,347 B1 * 12/2001 Hunter et al. ........... 514/449
6,759,431 B2 * 7/2004 Hunter et al. ........... 514/449
2003/0144570 A1 * 7/2003 Hunter et al. ............. 600/1

OTHER PUBLICATIONS

Kobayashi et al., Effects of Taxoids from Taxus Cuspida on Microtubule Depolymerization and Vincristine Accumulation in MDR Cells, Bioorganic & Medical Chemistry Letters, 1997, vol. 7, No. 4, pp. 393-398.*
Gura, "Cancer Models: Systems for identifying New Drugs are Often Faulty", Science, vol. 278, No. 5340, pp. 1041-1042 (1997).*
Georg et al., "Semisynthesis and Biological Evaluation of Brevifoliol 13-[N-Benzoyl-(2'R, 3'S)-3'-phenylisoserinate", Bioorganic & Medicinal Chemistry Letters, vol. 3, No. 6, pp. 1349-1350 (1993).*

* cited by examiner

*Primary Examiner*—Frederick Krass
(74) *Attorney, Agent, or Firm*—Darby & Darby

(57) ABSTRACT

The present invention relates to the bioactivity of taxanes isolated from the leaves of Himalayan Yew tree *Taxus wallichiana* against human cancer cell lines grown in-vitro and subsequent identification of brevifoliol [1] as anticancer agent useful in the treatment of various types of cancer in humans

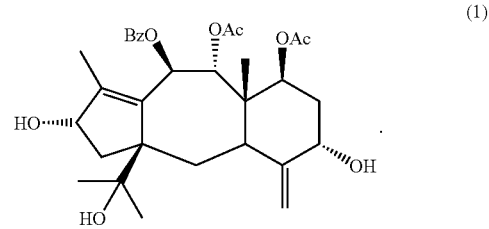
(1)

8 Claims, 1 Drawing Sheet

PHARMACEUTICAL COMPOSITION CONTAINING BREVIFOLIOL FOR USE IN CHEMOTHERAPEUTIC TREATMENT OF HUMAN BEINGS, METHOD THEREFOR

FIELD OF THE INVENTION

The present invention relates to a method for the chemotherapeutic treatment of human beings using brevifoliol. More particularly, the present invention relates to the use of brevifoliol for the treatment human cancer lines. The present invention also relates to the bioactivity testing of taxanes from the leaves of Himalayan Yew tree *Taxus wallichiana* against human cancer cell lines grown in-vitro and subsequent identification of brevifoliol [1] as anticancer agent useful in the treatment of various types of cancer in humans. The present invention also relates to a pharmaceutical composition containing brevifoliol and a pharmaceutically acceptable carrier for the chemotherapeutic treatment of human beings.

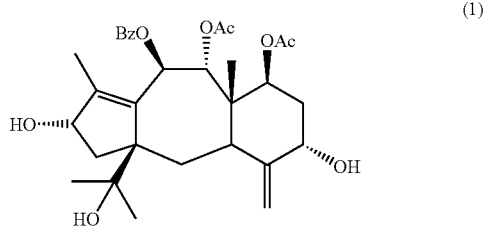

(1)

BACKGROUND OF THE INVENTION

In 1971, a novel compound isolated from the bark of the northwest Pacific yew tree, *Taxus brevifolia* Nutt. was described by Wani M. C. et al (in 1971, J.Am.Chem.Soc. 93, 2325–2327). This compound, named taxol (also known in the literature as paclitaxel) demonstrated moderate in vivo activity against the P-388, P-1534, and L-1210 murine leukaemia, the Walker 256 carcino-sarcoma, sarcoma 180, and Lewis lung tumor test systems. Taxol has a wide spectrum of anticancer activity. It has been approved by the Food and Drug Administration of United States in 1992 for the treatment of ovarian cancer and again in 1994 for the treatment of breast cancers. It has also been found to be effective against leukemia, and cancer of the head, neck, endometrium and lungs. Recently, it has also been used to treat polycystic kidney disease which accounts for ten percent of the kidney transplant among the dialysis patients (Nature p.750, 1994).

In more than twenty years since the initial report of its isolation, structure elucidation, and bioactivity, taxol has garnered support as an anticancer agent, culminating in recent FDA approval of its use against breast and ovarian cancers. There are two main reasons for the attention directed toward this drug. First, it shows promise against refractory breast and ovarian cancers, which are difficult to treat and which are responsible for the deaths of 60,000 women every year (Chemical &Engineering News 1991, (September), 11–18). Second, it exhibits a mode of action, which is unique among cancer chemotherapeutic agents. Unlike known antimicrotubule agents, which block microtubule production, taxol promotes tubulin polymerisation and stabilizes microtubules against depolymerization (Schiff P. B., et al. 1979, Nature 277, 665–667). Microtubules are important subcellular target for chemotherapeutic agents. Antimicrotubule agents, including the Vinca (*Catharanthus*) alkaloids, are extremely potent, requiring only a few molecules to disrupt the microtubular structure of cancer cells. The discovery of a new compound targeting these structures is of particular importance.

Despite its promise, there is a problem with taxol. This highly functionalised diterpene is isolated from inner bark of relatively rare and slow growing Pacific yew tree *Taxus brevifolia*, and few related species in extremely small quantities (<0.02% dry wt) (Chemical &Engineering News 1991, (September), 11–18). Himalayan yew, *Taxus wallichiana* Zucc. is a tree or a large shrub distributed in the north temperate zone of the Indian subcontinent (The Wealth of India (1976), A dictionary of Indian raw materials and industrial products, Vol. X, CSIR publication, New Delhi, P.132–134.). In contrast to the European yew (*T. baccata* Linn.), the Himalayan yew has a remarkable history of medicinal uses. The leaves of the Himalayan yew are used for treatment of hysteria, epilepsy, nervousness and as a lithic in calculus complaints while its non-poisonous fleshy arils have carminative, expectorant and stomachic properties (The Wealth of India (1976), p.132–134). In addition to the above medicinal properties, Himalayan yew (*Taxus wallichiana*) also contains the potent anticancer drug taxol and its important precursor 10-deacetyl baccatin III (DAB).

The currently practiced procedures for isolating taxol from bark have the disadvantages of being fatal to the source, being very difficult to carry out, and producing low yields. For example, (Vidensek et al 1990; *Journal of Natural Products* 53, 1609–1610) a 0.01% yield from a large-scale isolation starting with 806 lbs. or more of *Taxus brevifolia* bark has been reported. Similar procedures have been reported which comparably produce low yields, ranging from as low as 0.004%, up to about (but not above) 0.017%. A yield of 0.01% translates into 1 g being isolated from 10 kg of the bark, or 1 kg of taxol from 10,000 kg (approx.22,000 lbs) of the bark. A mature tree is said to yield 20–25 lbs. of bark, and this means that nearly 800–1000 trees are needed to produce a kilogram of taxol. Reported yields of taxol from various species of yew tree range from 50 mg/kg to 165 mg/kg (i.e., 0.005–0.017%). At present, bark of *Taxus brevifolia* is still being used as the major source of taxol. Because of (a) the low (0.01% or less) yields of taxol from the bark, (b) the relative unavailability of any other useful analogues, and (c) the need to cut the slow-growing trees to harvest the bark, it was decided that the bark was not an attractive source for taxol. Therefore, besides isolation from the bark, there are currently three avenues that are being pursued for the future production of taxol: (1) isolation from renewable plant parts, e.g., the ornamental yew clippings and needles; (2) semi-synthesis of taxol; (3) production of taxol by tissue culture procedures and (4) to find new taxanes from needles which are a renewable source of supply with anticancer properties.

The aim of present invention was to isolate different types of taxanes other than taxol, from the leaves commonly called 'needles' of *Taxus wallichiana* and evaluate their anticancer potential. In the course of these investigations a taxane brevifoliol [1] was identified which showed promising anticancer activity against in-vitro grown human cancer cell lines.

OBJECTS OF THE INVENTION

The main object of the invention is to provide a composition for the chemotherapeutic treatment of human beings.

It is another object of the invention to provide a method for the chemotherapeutic treatment of human beings using brevifoliol, a taxane isolated from various *Taxus* species.

It is another object of the invention to provide a method for the treatment of human cancer lines using brevifoliol, a taxane isolated from various *Taxus* species.

SUMMARY OF THE INVENTION

The present invention provides bioactivity testing of various taxanes isolated from leaves of Himalayan Yew tree *Taxus wallichiana* against human cancer cell lines grown in-vitro and subsequent identification of brevifoliol [1] as anticancer agent useful in the treatment of various types of cancer such as ovarian (PA-1), colon (Caco-2), breast (MCF-7) and oral (KB-403) cancer cells where the IC90 values are comparatively similar or even less than that of standard drug 'taxol'. Brevifoliol is used as a cancer chemotherapeutic agent.

Accordingly, the present invention provides a composition for chemotherapeutic treatment of human beings, comprising a pharmaceutically effective amount of brevifoliol of the formula 1 and a pharmaceutically acceptable carrier.

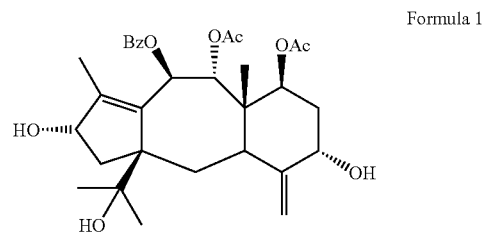

Formula 1

In one embodiment of the invention, the amount of brevifoliol is in the range of 0.004 to 20 µg/ml.

The present invention also provides a method for the chemotherapeutic treatment of human beings comprising administering to a patient suffering from cancer, a therapeutically effective amount of brevifoliol of the formula 1

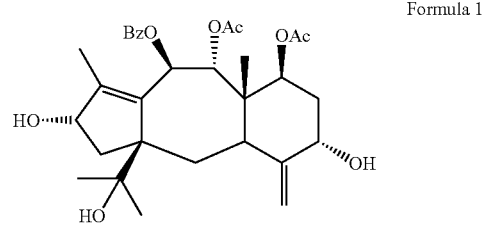

Formula 1 along with a pharmaceutically acceptable carrier.

In one embodiment of the invention, the concentration of brevifoliol is in the range of 0.004 to 20 µg/ml.

In yet another embodiment of the invention, the pharmaceutically acceptable carrier does not interfere with the activity of brevifoliol.

In yet another embodiment of the invention, the chemotherapeutic treatment is limited to ovarian, colon, breast and oral cancers.

The invention also provides a method for treatment of human cancer lines comprising administering to a patient a therapeutically effective amount of brevifoliol of the formula 1

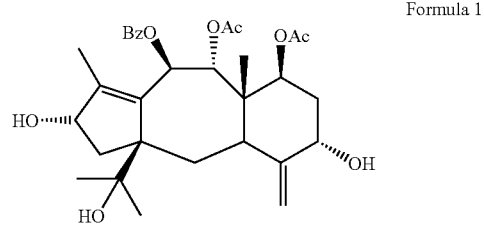

Formula 1 along with a pharmaceutically acceptable carrier.

In one embodiment of the invention, the concentration of brevifoliol is in the range of 0.004 to 20 µg/ml.

In yet another embodiment of the invention, the pharmaceutically acceptable carrier does not interfere with the activity of brevifoliol.

In yet another embodiment of the invention, the human cancer lines are selected from the group consisting of ovarian (PA-1), colon (Caco-2), breast (MCF-7) and oral (KB-403) cancer cells.

The present invention also provides for the use of brevifoliol of the formula 1

Formula 1 along with a pharmaceutically acceptable carrier for the chemotherapeutic treatment of human beings.

In one embodiment of the invention, the concentration of brevifoliol is in the range of 0.004 to 20 µg/ml.

In yet another embodiment of the invention, the pharmaceutically acceptable carrier does not interfere with the activity of brevifoliol.

In yet another embodiment of the invention, the chemotherapeutic treatment is limited to ovarian, colon, breast and oral cancers.

The invention also provides for the use of brevifoliol of formula 1

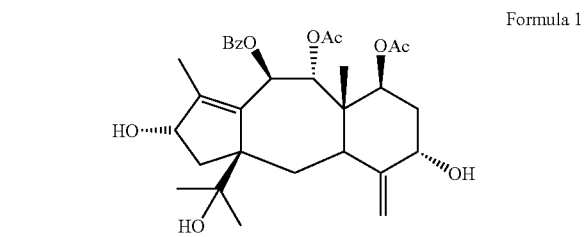

Formula 1 along with a pharmaceutically acceptable carrier for chemotherapeutic treatment of human beings.

In one embodiment of the invention, the concentration of brevifoliol is in the range of 0.004 to 20 µg/ml.

In yet another embodiment of the invention, the pharmaceutically acceptable carrier does not interfere with the activity of brevifoliol.

In yet another embodiment of the invention, the human cancer lines are selected from the group consisting of ovarian (PA-1), colon (Caco-2), breast (MCF-7) and oral (KB-403) cancer cells.

DETAILED DESCRIPTION OF THE INVENTION

Figure 1:
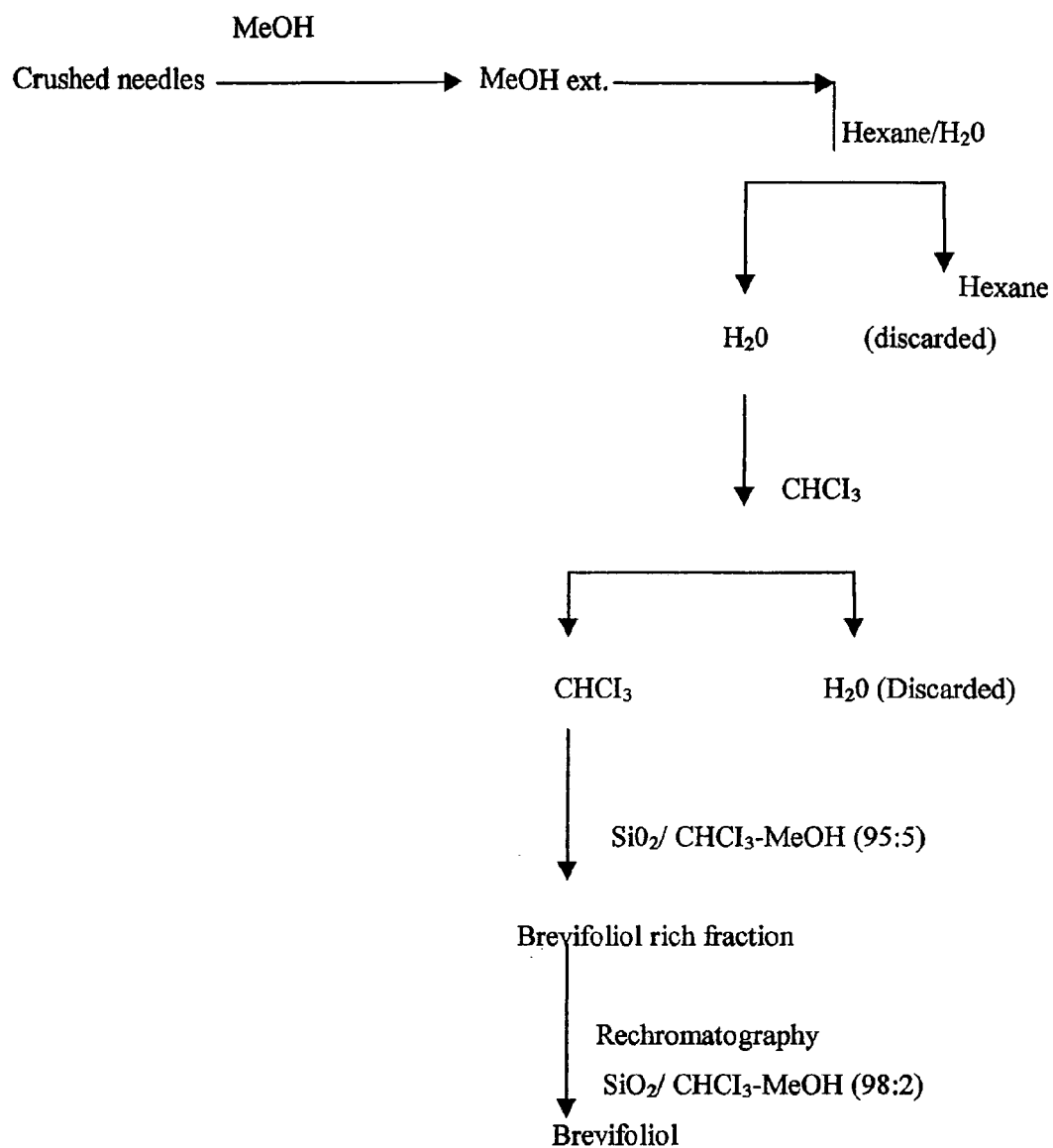
FIG. 1 is a flowchart depicting the reaction mechanism for the isolation of brevifoliol described in Example 3.

As a part of the studies on the isolation of anticancer compounds a number of taxanes were isolated from the needles of the plant *Taxus wallichiana* and tested for their anti-cancer properties against six human cancer cell lines in-vitro. The bioactivity testing was done at two stages. In the initial step, MTT assay was performed from which the inhibitory concentration ($IC_{90}$) the concentration (μg/mL) of the taxanes required for 90% inhibition of cell growth was deduced. Further, the compounds, which showed cell growth inhibitory activity was evaluated in the clonogenic assay. The MTT assay cannot discriminate between growth inhibition and cell death; it is an overall measurement of cell proliferation (Woerdenbag et al., 1993; *J.Nat.Prod*. 56 (6): 849–856). Therefore the $IC_{90}$ data obtained by the MTT assay may overestimate the cell killing activity of a compound. Hence, the clonogenic assay for tumor cells which determines the actual cell death was performed to determine the cytotoxic potential of test compounds. Persons skilled in the art of anti-cancer drug discovery can perform both these assays.

The data obtained in these bioassays against human cancer cells indicated that brevifoliol was highly inhibitory to ovarian (PA-1), colon (Caco-2), breast (MCF-7) and oral (KB-403) cancer cells where the IC90 values were comparatively similar or even less than that of standard drug 'taxol'. Thus brevifoliol can be used as cancer chemotherapeutic agent.

Brevifoliol was first isolated from the leaves (also referred as 'needles') of the plant *Taxus brevifolia* (Balza et al *Phytochemistry* 30, p.1613–1614; 1991). The process of its isolation involved extracting the fresh leaves of *Taxus wallichiana* with ethyl alcohol to get an extract. The crude extract after concentration was diluted with water and partitioned between hexane, chloroform and ethyl acetate sequentially. The chloroform extract upon concentration yielded a dark brown residue. The resultant residue was subjected to column chromatography over silica gel and eluted with chloroform and chloroform-methanol gradient. Six fractions were collected and brevifoliol was isolated from fraction five by rechromatography over silica gel and eluting with hexane-ethyl acetate gradient.

Brevifoliol has been isolated from other species of *Taxus* including the Himalayan yew tree *Taxus wallichiana* that is available in India. Recently, the structure of brevifoliol has been revised and it was shown to belong to 11 (15–1) abeo taxoid bicyclic skeleton of formula [1]. For this invention, brevifoliol was also isolated from the leaves of the plant following a process which involved extracting the dried and crushed needles of *Taxus wallichiana* with methanol for 72 hours and the extract was concentrated in vacuo. The concentrate was diluted with water and extracted with hexane and chloroform respectively. Concentration of the chloroform phase under vacuum left a residue, which was separated by column chromatography over silica gel. Fraction eluted with chloroform-methanol (98:5) contained brevifoliol, which was further purified by rechromatography over silica gel and eluted with chloroform-methanol (99:2). Fractions containing brevifoliol were combined and concentrated and recrystallized from pet-ether and ethyl acetate mixture to get brevifoliol as needles (Chattopadhyay et al (1996) *Indian J. Chemistry* 35B, 175–177).

The following examples further illustrate the invention and should not be construed as limiting the scope of the invention.

EXAMPLES

Example 1

In-vitro Anticancer MTT Assay

The following six human cancer lines were procured from the Cell Repository of the National Center for Cell Sciences (NCSS) at Pune. Their corresponding ATCC No. and the organ from which they were isolated are also mentioned in Table 1 below:

TABLE 1

Description of human cancer cell lines and their ATCC Nos.

| Cancer Cell Line | Source organ | Type | ATCC No. |
| --- | --- | --- | --- |
| COLO-320DM | Colon cancer | Suspension | CCL-220 |
| KB-403 | Mouth cancer | Adherent | CCL-17 |
| WRL-68 | Liver cancer | Adherent | CL-48 |
| PA-1 | Ovary cancer | Adherent | CRL-1572 |
| MCF-7 | Breast cancer | Adherent | HTB-22 |
| CaCO2 | Colon cancer | Adherent | — |

Cytotoxicity testing in vitro was done by the method of Woerdenbag et al.,1993; *J.Nat.Prod*. 56 (6): 849–856). $2 \times 10^3$ cells/well were incubated in the 5% $CO_2$ incubator for 24 h to enable them to adhere properly to the 96 well polysterene microplate (Grenier, Germany). Test compounds dissolved in 100% DMSO (Merck,Germany) in at least five doses were added and left for 6 h after which the compound plus media was replaced with fresh media and the cells were incubated for another 48 h in the $CO_2$ incubator at 37° C. The concentration of DMSO used in our experiments never exceeded 1.25%, which was found to be non-toxic to cells. Then, 10 μl MTT [3-(4,5-dimethylthiazol-2-yl)-2,5-diphenyltetrazolium bromide; Sigma M 2128] was added, and plates were incubated at 37° C. for 4 h. 100 μl dimethyl sulfoxide (DMSO, Merck, Germany) were added to all wells and mixed thoroughly to dissolve the dark blue crystals. After a few minutes at room temperature to ensure that all crystals were dissolved, the plates were read on a SpectraMax 190 Microplate Elisa reader (Molecular Devices Inc., USA), at 570 nm. Plates were normally read within 1 h of adding the DMSO. The experiment was done in triplicate and the inhibitory concentration (IC) values were calculated as follows: % inhibition=[1-OD (570 nm) of sample well/OD (570 nm) of control well]×100. $IC_{90}$ is the concentration μg/mL required for 90% inhibition of cell growth as compared to that of untreated control. The results described in Table 2 indicate that brevifoliol is active against all cancer cell lines except liver cancer (WRL-68).

TABLE 2

Cytotoxic properties (IC 90 in µg/mL) of various taxanes isolated from
*T. wallichiana* against human cancer cells.

| Name of the Taxanes | PA-1 | Caco-2 | MCF-7 | KB-403 | COLO-320 DM | WRL-68 |
|---|---|---|---|---|---|---|
| Taxol (Std) | 0.9 | 0.065 | 0.85 | 0.047 | 0.01 | 2.5 |
| Doxorubicin (Std) | 0.5 | 0.052 | 0.01 | 0.06 | 0.08 | 1.0 |
| 2-deacetoxy taxinine J | — | 0.009 | 6.5 | 3.5 | 1.0 | — |
| Brevifoliol | 6.0 | 0.85 | 0.004 | 0.035 | 0.1 | >10.0 |
| 2-deacetoxy decinnamoyl taxinine J | 10.0 | 6.4 | — | 0.01 | >10.0 | 0.5 |
| 10,13,deacetyl abeobaccatin IV | — | — | >10.0 | >10.0 | — | — |
| Acetoxy brevifoliol | — | — | — | 10.0 | — | 5.0 |
| 2'-Deacetoxy austrospicatin | 4.0 | 1.0 | 3.5 | 4.5 | — | — |

Example 2

Soft Agar Assay For Colony Formation

The clonogenic assay for tumor cells which determines the actual cell death was performed to determine the cytotoxic potential of test compounds. The principle of clonogenic assay is to investigate the ability of an individual cell to form a colony on a soft agar plate containing various concentrations of test compounds.

Cells not able to form colonies are considered clonogenically dead (Beekman et al 1997; *J.Nat.Prod.* 60(4): 325–330). The concentration of test compound resulting in 90% of the control (untreated) colonies was denoted as $IC_{90}$ and was used as a parameter for cytotoxicity. The assay was performed as described previously except that the test compounds were added into the top soft agar and the cells were plated out to form colonies. Anthracycline derivative doxorubicin and microtubule depolymerization inhibitor paclitaxel (Sigma Chem. Co., St. Loius, USA) both established anticancer agents were included as standard reference drugs.

TABLE 3

Cytotoxic properties (IC 90 in µg/mL) of various taxanes isolated from
*T. wallichiana* against human cancer cells.

| Name of the Taxanes | PA-1 | Caco-2 | MCF-7 | KB-403 | COLO-320 DM | WRL-68 |
|---|---|---|---|---|---|---|
| Taxol (Std) | 1.47 | 1.99 | 1.99 | 7.94 | 0.8 | 6.3 |
| Doxorubicin (Std) | 10.0 | 0.079 | 0.8 | — | 0.1 | 3.98 |
| 2-deacetoxy taxinine | — | 0.25 | 7.94 | 28.18 | 10.0 | — |
| Brevifoliol | 7.94 | 0.31 | 1.99 | 0.398 | 1.0 | 15.84 |
| 2-deacetoxy decinnamoyl taxinine J | 15.84 | 31.82 | — | 0.11 | — | 12.58 |
| 10,13,deacetyl abeobaccatin IV | — | — | — | — | — | — |
| Acetoxy brevifoliol | — | — | — | 1.0 | — | 7.0 |
| 2' Deacetoxy austrospicatin | 6.3 | 3.16 | 5.63 | 0.44 | — | — |

Example 3

Chemical Process for the Isolation of Brevifoliol

Dried and crushed needles of *Taxus wallichiana* (1 kg) were extracted with methanol (3×3 L) for 72 hours and concentrated in vacuo. The concentrate was diluted with water and extracted with hexane (1 L) and chloroform (1 L) respectively. Concentration of the chloroform phase under vacuum left a residue (12 g), which was separated by column chromatography over silica gel. Fraction eluted with chloroform-methanol (95:5) contained brevifoliol, which was further purified by re-chromatography over silica gel and eluted with chloroform-methanol (98:2). Fractions containing brevifoliol were concentrated under vacuum and brevifoliol was obtained as amorphous solids, (50 mg).

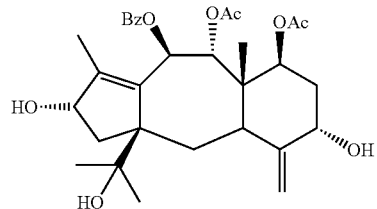

Brevifoliol was crystallized from petroleum ether-acetone mixture as needles. Brevifoliol, mp 200–201° C., $[\alpha]_D$–25° C. (c 1, MeOH) was characterized on the basis of its reported spectral data and by direct comparison with an authentic sample (Chattopadhyay, S. K. et al, Indian J. Chemistry 35B, 175–177 (1996)).

We claim:

1. A pharmaceutical composition for the chemotherapeutic treatment of human beings suffering from cancer, comprising a therapeutically effective amount of brevifoliol of formula 1

Formula 1 along with a pharmaceutically acceptable carrier;
wherein said cancer is selected from COLO-320DM colon cancer, KB-403 oral cancer, PA-1 ovarian cancer, MCF-7 breast cancer, and CaCO2 colon; and
wherein the concentration of brevifoliol in said composition is in the range of 0.004 to 20 µg/ml.

2. A method for the chemotherapeutic treatment of human beings comprising administering to a cancer patient, a therapeutically effective amount of a composition comprising brevifoliol of formula 1

Formula 1

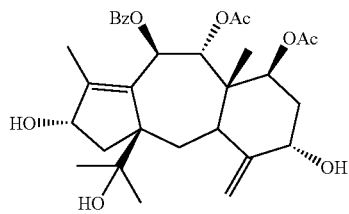

along with a pharmaceutically acceptable carrier;
wherein said cancer is selected from COLO-320DM colon cancer, KB-403 oral cancer, PA-1 ovarian cancer, MCF-7 breast cancer, and CaCO2 colon cancer.

3. A method as claimed in claim 2 wherein the concentration of brevifoliol in said composition is in the range of 0.004 to 20 µg/ml.

4. A method as claimed in claim 2 wherein the pharmaceutically acceptable carrier does not interfere with the activity of brevifoliol.

5. A method of inhibiting a human cancer cell line comprising contacting said cancer cell line with an effective amount of a composition comprising brevifoliol of the formula 1

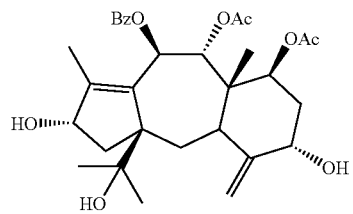

along with a pharmaceutically acceptable carrier;
wherein said cancer cell line is selected from colon (COLO-320DM and CaCO2), oral (KLB-403), ovarian (PA-1), and breast (MCF-7) cell lines.

6. A method as claimed in claim 5 wherein the concentration of brevifoliol in said composition is in the range of 0.004 to 20 µg/ml.

7. A method as claimed in claim 5 wherein the pharmaceutically acceptable carrier does not interfere with the activity of brevifoliol.

8. A method as claimed in claim 5 wherein the human cancer line is selected from ovarian (PA-1), colon (Caco-2), breast (MCF-7) and oral (KB-403) cell lines.

* * * * *